United States Patent [19]

Morgan

[11] Patent Number: 5,278,060
[45] Date of Patent: Jan. 11, 1994

[54] METHOD FOR PRODUCING THE NLA III RESTRICTION ENDONUCLEASE AND METHYLASE

[75] Inventor: Richard D. Morgan, Middleton, Mass.

[73] Assignee: New England Biolabs, Inc., Beverly, Mass.

[21] Appl. No.: 575,285

[22] Filed: Aug. 30, 1990

[51] Int. Cl.$^5$ .......................... C12N 9/22; C12N 9/10; C12N 15/55; C12N 15/54

[52] U.S. Cl. .................... 435/199; 435/69.1; 435/193; 435/252.3; 435/320.1; 536/23.2; 935/14; 935/19; 935/27; 935/66; 935/73

[58] Field of Search ...................... 435/69.1; 435/697, 172.1, 435/723, 252.3, 435/33, 320.1; 199; 536/27, 435/697, 172.3, 252.3, 252.33, 536/27

[56] References Cited

U.S. PATENT DOCUMENTS

| | | | |
|---|---|---|---|
| 4,983,522 | 1/1991 | Barsomian et al. | 435/172.3 |
| 4,983,542 | 1/1991 | VanCott et al. | 435/172.3 |
| 5,015,581 | 5/1991 | Benner et al. | 435/172.3 |
| 5,030,569 | 7/1991 | Lannen et al. | 435/172.3 |
| 5,053,330 | 10/1991 | Lannen et al. | 435/172.3 |
| 5,075,232 | 12/1991 | Morgan | 435/199 |
| 5,082,784 | 1/1992 | Chatterjee et al. | 435/252.3 |
| 5,147,800 | 9/1992 | Hammond et al. | 435/252.3 |

FOREIGN PATENT DOCUMENTS

| | | | |
|---|---|---|---|
| 193413 | 9/1986 | European Pat. Off. | 435/172.3 |
| 0248678 | 12/1987 | European Pat. Off. | |
| 0355981 | 2/1990 | European Pat. Off. | |

OTHER PUBLICATIONS

Barnes, G., and Rine, J., 1985, Proceedings of the National Academy of Sciences, USA, 82:1354–1358.
Kwoh, T. J., et al., 1986, Proceedings of The National Academy of Sciences, USA, 83:7713–7717.
Kwoh, T. J., et al., 1988, Nucleic Acids Research, 16(24):11489–11505.
Herman, J., et al., 1989, Journal of Cell Biochemistry, Supplement: 223, No. CH509.
Herman, J., et al., 1989, Proceedings of The American Association for Cancer Research, 30: 428, Abstract No. 1699.
Sullivan, K. M., et al., 1987, FEMS Microbiology Letters, 44(3): 389–393.
Karreman, C., et al., 1988, Journal of Bacteriology 170(6):2527–2536.
Endow, et al. J. Mol. Biol. 112:521 (1977).
Waalwijk, et al. Nucleic Acids Res. 5:3231 (1978).
Gingeras & Brooks Proc. Natl. Acad. Sci. USA 80:402–406 (1983).
Mann, et al. Gene #: 97–112 (1978).
Kosykh et al., Molec. Gen. Genet. 178:717–718 (1980).
Walder, et al. Proc. Nat. Acad. Sci USA 78:1503–1507 (1981).
Bougueleret, et al. Nucleic Acids Res. 121:3659–3676 (1984).
Theriault & Roy Gene 19:355–359, (1982).
Blumenthal, et al. J. Bacteriol 164:501–509, (1985).
Howard, et al. Nucleic Acids Res. 14:7939–7951 (1986).
Wilson, Gene 74:281–289 (1988).
Wilson, Trends in Genetics 4:314–318 (1988).
Lunnen, et al. Gene 74:25–32 (1988).
Chandrasegeran et al. Structure & Expression, vol. 1, pp. 149–156 Adenine Press (1988).
Brooks, et al. Gene 74:13 (1988).
Quiang & Schildkraut, Nucleic Acids Res. 14:1991–1999 (1986).
Birnboim & Doly, Nucleic Acids Res. 7:1513 (1979).
Wilson, G. Nucleic Acids Research vol. 19, No. 10, pp. 2539–2572 (1991).
Labbe, et al. Molecular & General Genetics, vol. 224, No. 1, pp. 101–110 (1990).

Primary Examiner—Robert A. Wax
Assistant Examiner—William W. Moore
Attorney, Agent, or Firm—Gregory D. Williams; David G. Conlin

[57] ABSTRACT

Recombinant DNA encoding the Nla III restriction endonuclease and modification methylase, and methods for the production of these enzymes from said recombinant DNA.

14 Claims, 6 Drawing Sheets

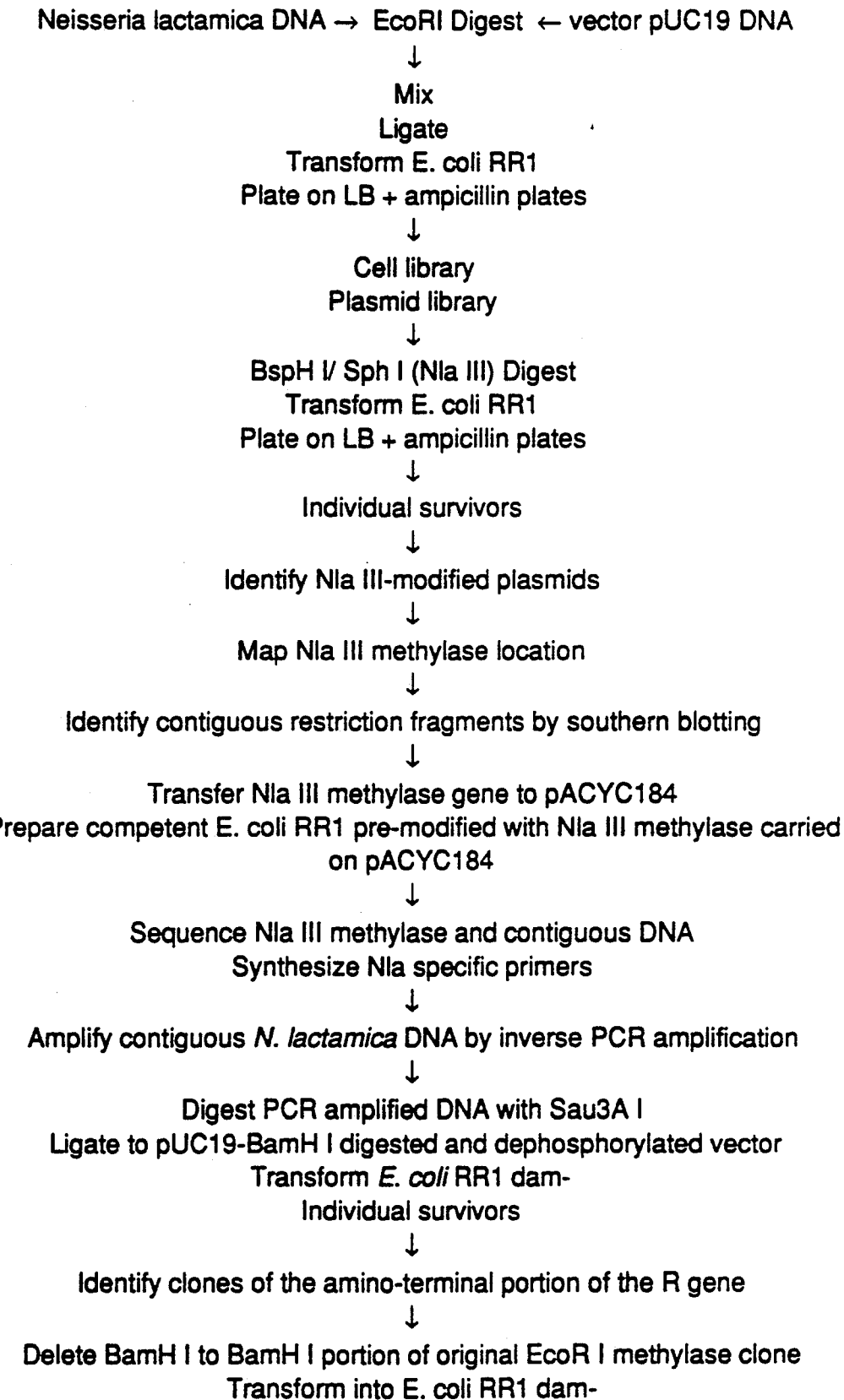
FIG. I

METHOD FOR PRODUCING THE NLA III RESTRICTION ENDONUCLEASE AND METHYLASE

BACKGROUND OF THE INVENTION

The present invention relates to recombinant DNA encoding the Nla III restriction endonuclease and modification methylase, and to methods for the production of these enzymes from said recombinant DNA.

Many bacteria contain systems which guard against invasion of foreign DNA. Bacterial cells contain specific endonucleases that make double-strand scissions in invading DNA unless the DNA has been previously modified, usually by the corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Three distinct types of R-M systems have been characterized on the basis of the subunit compositions, cofactor requirements, and type of DNA cleavage. Type I R-M systems are the most complex. The endonuclease typically contains three different types of subunits and requires $Mg^{++}$, ATP, and S-adenosyl-methionine for DNA cleavage. Their recognition sites are complex, and DNA cleavage occurs at non-specific sites anywhere from 400-7000 base pairs from the recognition site.

Type III R-M systems are somewhat less complex. The endonuclease of type III R-M systems contain only two types of subunits, and although $Mg^{++}$ and ATP are required for DNA cleavage, S-adenosyl-methionine stimulates enzymatic activity without being an absolute requirement. DNA cleavage occurs distal to the recognition site by about 25-27 base pairs.

Type II R-M systems are much simpler than either types I or III. The endonuclease only contains one subunit, and only $Mg^{++}$ is required for DNA cleavage. Moreover, the DNA cleavage site occurs within or adjacent to the enzyme's recognition site. It is this class of restriction endonucleases that has proved most useful to molecular biologists.

Bacteria usually possess only a small number of restriction endonucleases per species The endonucleases are named according to the bacteria from which they are derived Thus, the species *Haemophilus aegyptius*, for example, synthesizes three different restriction endonucleases, named Hae I, Hae II and Hae III. These enzymes recognize and cleave the sequences (AT)GGCC(AT), PuGCGCPy and GGCC respectively. *Escherichia coli* RY13, on the other hand, synthesizes only one enzyme, EcoR I, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4-6 nucleotides in length. More recently, recognition endonucleases having recognition sequences of 7-8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes." Some restriction endonucleases have degenerate or relaxed specificites in that they can recognize multiple bases at the same positions. EcoRI, which recognizes the sequence GAATTC is an example of a restriction endonuclease having a symmetrical relationship, while HaeII, which recognizes the sequence PuGCGCPy, typifies restriction endonucleases having a degenerate or relaxed specificity. Endonucleases with symmetrical recognition sites generally cleave symmetrically within or adjacent the recognition site, while those that recognize asymmetric sites tend to cut at distance from the recognition site, typically from about 1-13 base pairs away from that site.

The second component of bacterial R-M systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or more of the nucleotides within the sequence by the addition of a methyl group. Following methylation, the recognition sequence is no longer bound or cleaved by the corresponding restriction endonuclease. The DNA of a bacterial cell is always modified by virtue of the activity of its modification methylase, and it is therefore insensitive to the presence of the endogenous restriction endonuclease. It is only unmodified, and therefore identifiably foreign DNA that is sensitive to restriction endonuclease recognition and attack.

More than 1000 different restriction endonucleases have been isolated from bacterial strains, and many share common specificites. Restriction endonucleases which recognize identical sequences are called "isochizomers." Although the recognition sequences of isochizomers are the same, they may vary with respect to site of cleavage (e.g., Xma I J. Sma I Endow et al., *J.Mol.-Biol* 112:521 (1977) Waalwijk et al., *Nucleic Acids Res.* 5:3231 (1978)) and in cleavage rate at various sites (Xho I v. Pae R7I Gingeras et al., *Proc. Natl. Acad. Sci U.S.A.* 80:402 (1983)).

With the advent of genetic engineering technology, it is now possible to clone genes and to produce the proteins and enzymes that they encode in greater quantities than are obtainable from their natural sources by conventional purification techniques.

Type II restriction-modification systems are being cloned with increasing frequency. Four methods are being used to clone R-M systems into *E. coli*: (1) subcloning of natural plasmids; (2) selection based on phage restriction; (3) selection based on vector modification; and (4) multi-step isolation.

The first cloned systems used bacteriophage infection as a means of identifying or selection restriction endonuclease clones (Hha II: Mann, et al., Gene 3: 97–112, (1978); EcoR II: Kosykh, et al., Molec. Gen. Genet. 178: 717–719, (1980); Pst I: Walder, et al., Proc. Nat. Acad. Sci. USA 78: 1503–1507, (1981)). Since the presence of R-M systems in bacteria enables them to resist infection by bacteriophages, cells that carry cloned R-M genes can, in principle, be selectively isolated as survivors from libraries that have been exposed to phage. This method has been found, however, to have only limited value. Specifically, it has been found that cloned R-M genes do not always manifest sufficient phage resistance to confer selective survival.

Subcloning of natural plasmids involves transferring systems initially characterized as plasmid-borne into *E. coli* cloning plasmids (EcoRV: Bougueleret, et al., Nucleic Acids Res. 12: 3659-3676, (1984); paeR7: Gingeras and Brooks, Proc. Natl. Acad. Sci USA 80: 402-406, (1983); Theriault and Roy, Gene 19: 355-359, (1982); Pvu II: Blumenthal, et al., J. Bacteriol. 164: 501-509, (1985)). In this approach the plasmids are purified prior to digestion and ligation, so reducing the complexity of the source DNA. Isolating the system then involves sub-cloning and characterizing libraries and perfoming selections. This approach also has a number of limitations including that most R-M systems are located on the bacterial chromosomal, not plasmids.

Vector modification, the most successful approach to date, is predicated on the assumption that the restriction and modification genes of a particular type II system are linked and are expressed sequentially, methylase and then endonuclease. Thus, in a population of methylase positive clones, some clones should also carry the corresponding endonuclease gene. This approach, known as methylase selection, was first used successfully by Wilson, EPO Publication No. 0193413, to clone the Hae II, Taq I, Ban I, Hind III, Hinf I, and Msp I R-M systems.

A number of R-M systems, however, have required a multi-step cloning approach. For example, during acquisition of a new R-M system, it has been found that a number of cells face an establishment problem. Unless the methylase has a head start over the endonuclease, the cell is in danger of cleaving its own cellular DNA. *E. coli* appears to cope with this problem by repairing its DNA, and is able to assimilate to many cloned R-M systems without apparent trauma Not all systems are easily assimilated however. The Dde I and BamH I R-M systems, for example, could not be cloned in a single step; rather, three steps were required (Howard et al., Nucleic Acids Res. 14:7939-7951 (1988)). There are, in fact, many systems for which only the methylase gene has been cloned. These systems may be similar to BamH I and Dde I, and may require similar approaches.

While a number of clones have been obtained by one or more of the above-described methods, see, Wilson, Gene 74, 281-289 (1988), cloning of type II R-M systems is not without difficulty. In particular, the genetics of many R-M systems have been found to be more complex, and methylase positive clones obtained by, for example, vector modification have not yielded the corresponding endonuclease gene. See, Wilson, Trends in Genetics 4, 314-318 (1988); Lunnen et al., Gene 74, 25-32 (1988). In fact, numerous obstacles are encountered in the process of cloning R-M systems using vector modification. For example, in some systems, the methylase and endonuclease genes may not be linked or the endonuclease used to fragment the bacterial DNA may cut either or both of the R-M genes. In other systems, such as BamH I and Dde I, the methylase may not protect sufficiently against digestion by the corresponding endonuclease, either because of inefficient expression in the transformation host, or because of the inherent control mechanism for expression of the methylase and endonuclease genes, or for unknown reasons. Modification may also be harmful to the host cell chosen for transformation. The endonuclease sought to be cloned may not be available in sufficient purity or quantity for methylase selection. In many systems, difficulties are also encountered in expressing the endonuclease gene in a transformation host cell of a different bacterial species.

In spite of the difficulties in cloning the more complex Type II R-M systems, it has been possible to obtain some endonuclease genes by modifying the vector modification selection method (see Lunnen et al., op. cit.) and/or by using a multi-step cloning approach For example, formation of multiple libraries, construction of new cloning vectors, use of isochizomers for the methylase selection step, mapping of methylase and/or endonuclease genes to determine the corresponding DNA sequences for use as hybridization probes, and other variations to the above-described approaches have yielded a number of recalcitrant recombinant R-M systems.

However, at the outset of any type II R-M cloning project, one simply does not know which, if any, and what variations or modifications to previous approaches may be required to clone any particular R-M system. For example, the detailed genetics of the particular system is usually unknown. Type II R and M genes may be present on the genome in any of four possible arrangements. Wilson, Trends in Genetics, supra. The sizes of the enzymes, and of the corresponding genes, vary widely between one R-M system and another, as do the DNA and amino acid sequences. In fact, isochizomeric restriction endonucleases have been found to display few similarities. Id, at 318, see also Chandrasegeran et al., *Structure and Expression,* Vol. I, pp 149-156, Adenine Press (1988).

Mechanisms of control of R and M gene expression also vary widely among type II systems. For example, expression of the endonuclease gene may be modification-dependent, as is indicated in the Ava II, Hae II, Hinf I, PstI and Xba I systems. Alternatively, the endonuclease gene may contain a large number of its own recognition sites as compared to the corresponding methylase gene, as in the Taq I system. Id.

During transformation of cells to obtain clones carrying the target R-M system, cellular DNA is initially unmodified and consequently in danger of being digested by the target endonuclease. Transformation host cells must either contain DNA repair systems or be able to delay expression of the target endonuclease gene until modification is complete. If neither of these mechanisms is available to the transformation host, a problem is encountered in establishing the clones genes in the host. As noted above, when establishment problems were encountered in cloning the Dde I and BamH I systems, it was necessary to introduce the methylase and endonuclease genes sequentially, to protect the DNA of the transformation host cells (Howard, K. A. et al., supra, Brooks et al., Gene 74: 13 (1988)). However, some R-M systems have resisted all attempts to clone them, and others have yielded only the methylase gene, possibly because of establishment difficulties. Wilson, Trends in Genetics 4, 317.

It has been found that transformation host cells may also contain systems that restrict foreign types of modification. For example, two systems have been identified in *E. coli* which restrict modified DNAs: the mcr system restricts DNA containing methyl-cytosine, and the mrr system restricts DNA containing methyl-adenine. It is therefore usually necessary to use *E. coli* strains that are defective in these systems. The presence of additional host cell restriction systems may also be responsible for the difficulties encountered in cloning of R-M systems.

Because restriction endonucleases and modification methylases are useful tools for characterizing and rearranging DNA in the laboratory, there is a commercial incentive to produce the enzymes abundantly and in substantially pure form. Using recombinant DNA techniques in accordance with the present invention, the Nla III restriction endonuclease and modification methylase may be produced simply and in commercially useful amounts.

SUMMARY OF INVENTION

The present invention relates to the type II R-M system Nla III, which derives from *Neisseria lactamica* (NRCC 2118). Nla III recognizes the DNA sequence 5' CATG 3' and cleaves 3' of the G to produce a 4-base 3' extension, 5' CATG/ 3' (Qiang and Schildkraut, Nucleic Acids Res 14: 1991–1999, (1986), the disclosure of which is hereby incorporated by reference herein).

In accordance with the present invention there is provided recombinant DNA encoding the Nla III restriction endonuclease and modification methylase obtainable from *N. lactamica* (NRCC 2118), and methods for the production of the recombinant DNA encoding those enzymes. The present invention is further directed to methods for producing the Nla III restriction endonuclease and modification methylase in substantially pure form.

DETAILED DESCRIPTION OF THE INVENTION

Figure 1:
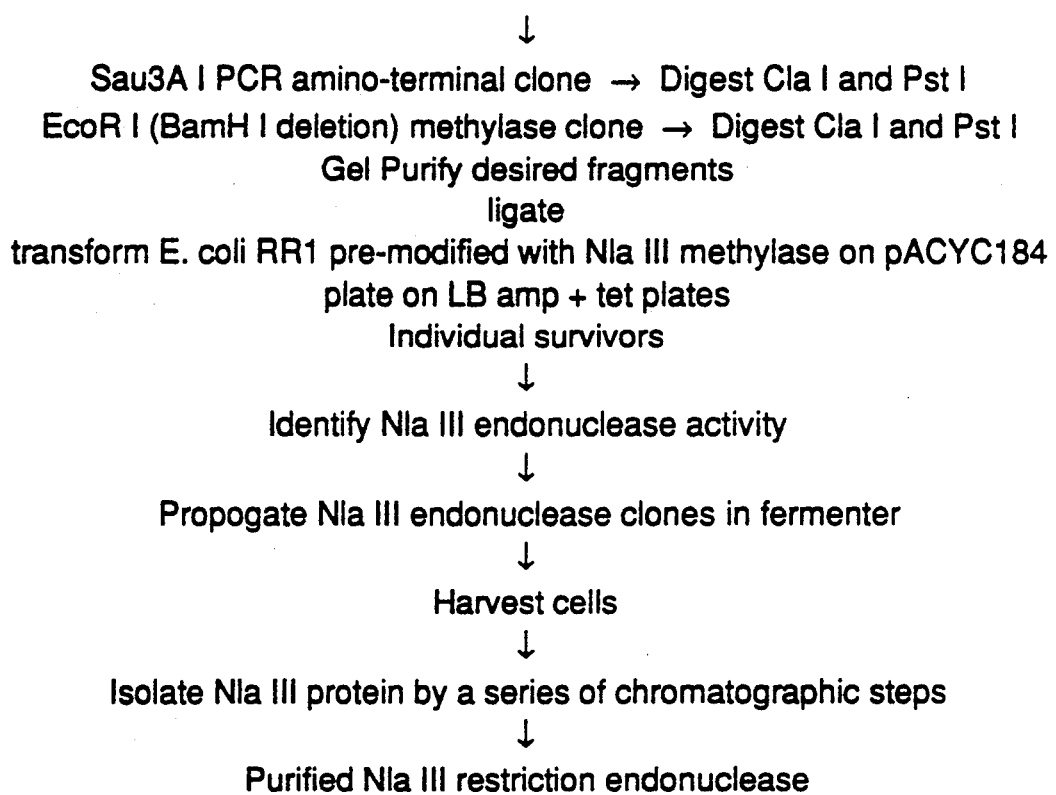
FIG. 1 illustrates the scheme for cloning and producing the Nla III restriction endonuclease.
Figures 1, 2:
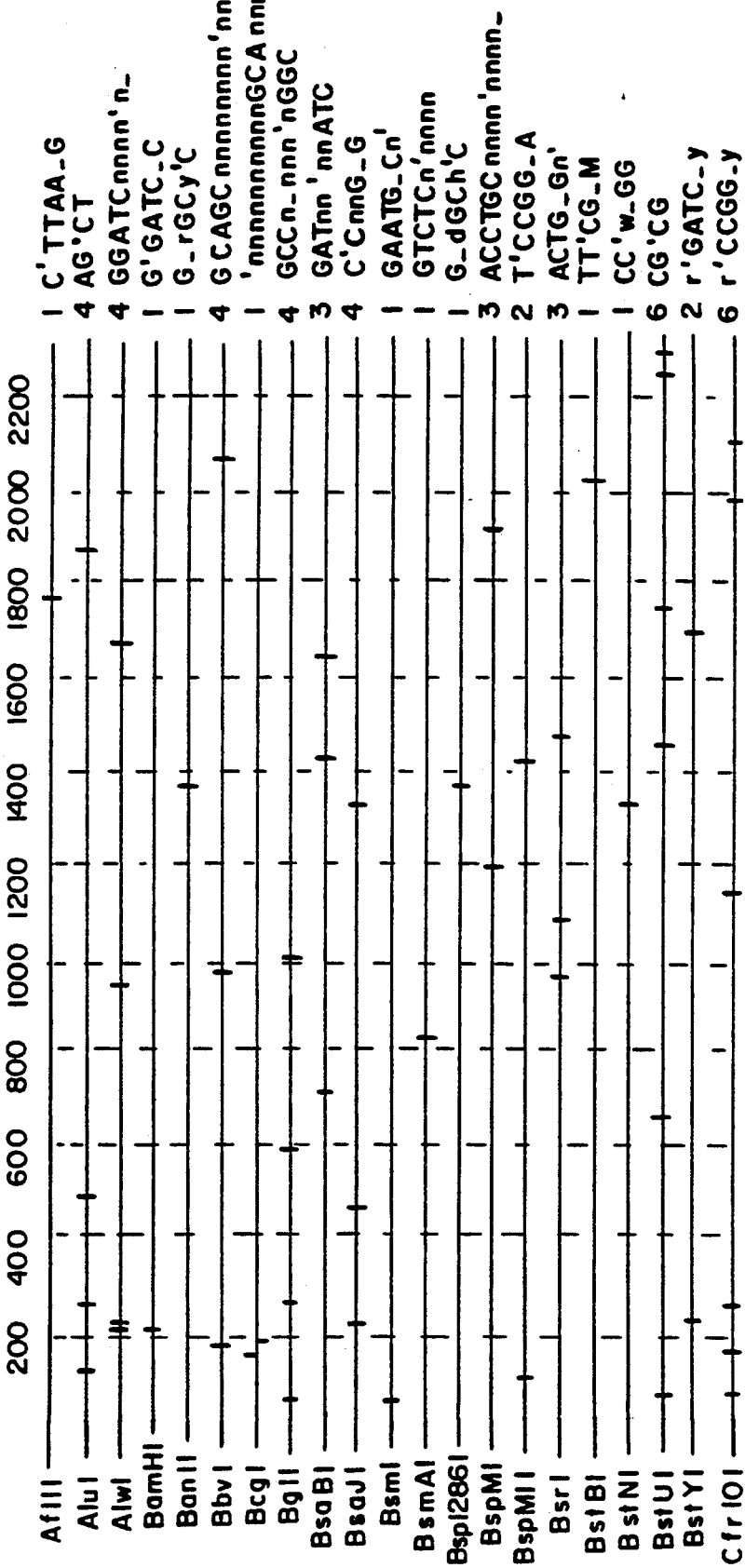
FIG. 2 is a restriction map of a fragment of *N. lactamica* DNA that encodes the Nla III restriction endonuclease and modification methylase. The fragment was cloned into the BamH I and Pst I sites of pUC19 (ATCC 37254) to create pRM125RM 100c-4.
Figure 2:
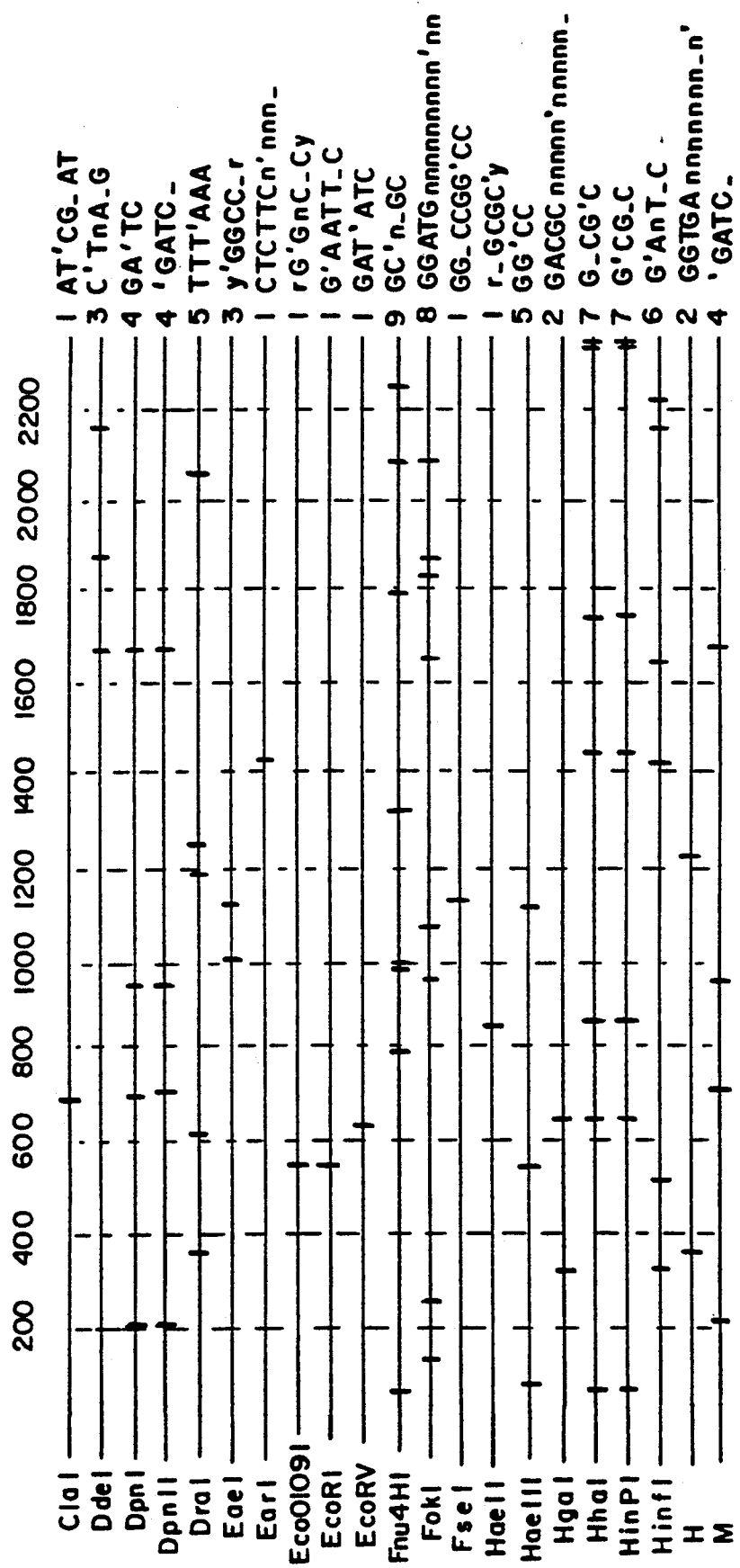
Figures 2, 3:
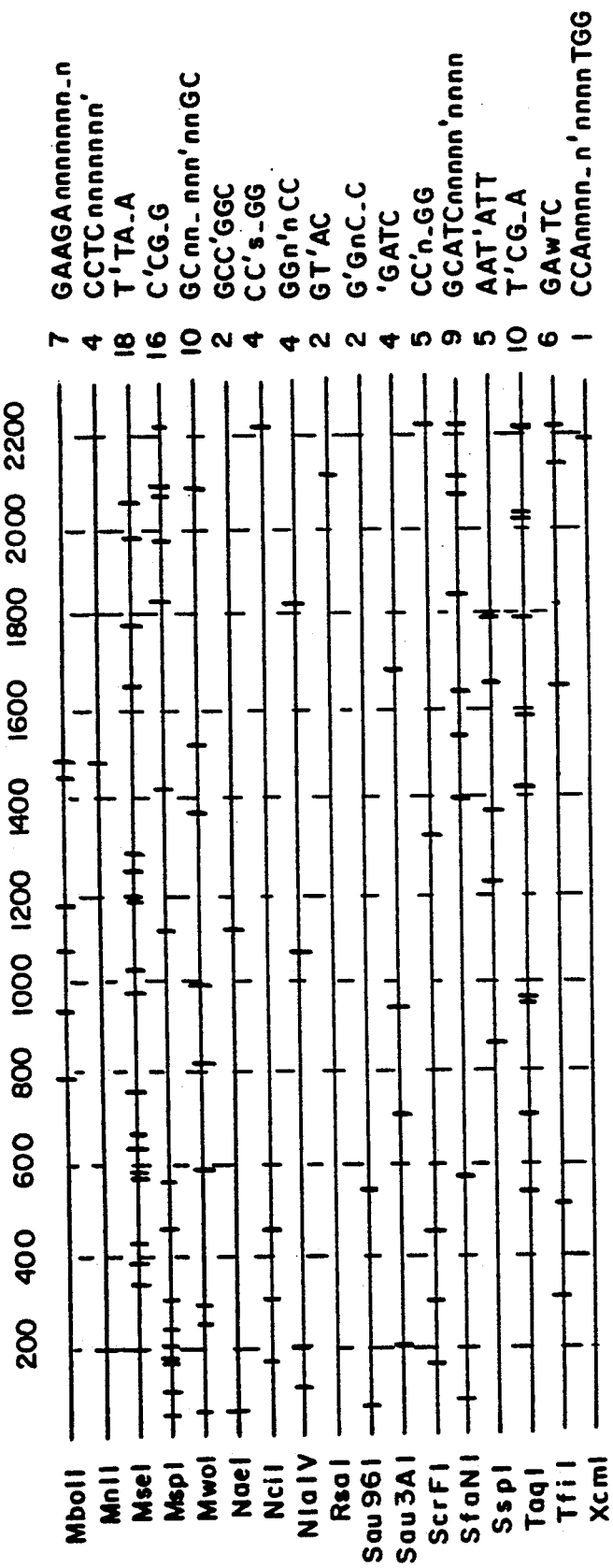
FIG. 3 is a photograph of an agarose gel demonstrating Nla III restriction endonuclease activity in cell extracts of *E. coli* RR1 (ATCC 31343) carrying pRM125RM 100c-4. Lanes 2 to 9 show serial dilution of a crude extract from Nla III clone NEB #576 in Nla III reaction buffer containing 20 ug/ml lambda DNA (NEB#301-1). 2.5 grams of cells were suspended in 10 mls of sonication buffer, disrupted by sonication and clarified by centrifugation. The dilutions are expressed in ul crude extract per ug of DNA in a reaction volume of 50 ul. Reactions were 1 hour at 37° C Lane 2; 9 ul, lane 3; 3 ul, lane 4; 1 ul, lane 5; 0.3 ul, lane 6; 0.1 ul, lane 7; 0.4 ul, lane 8; 0.01 ul, lane 9; 0.004 ul. Lanes 1 and 10; Hind III-lambda and Hae III-phiX174 size standards.
Figure 3:
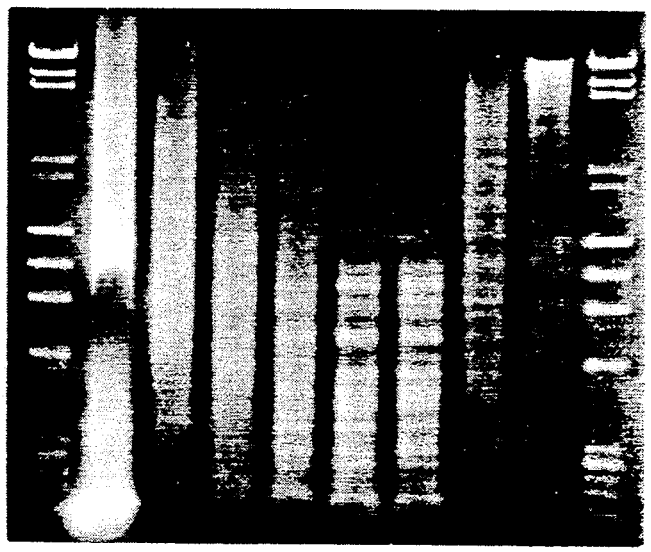

The present invention provides detailed methods for obtaining recombinant DNA encoding the Nla III restriction endonuclease and modification methylase, and for expressing recombinant DNA to obtain the corresponding enzymes. The recombinant DNA of the present invention may be transformed into appropriate bacterial host cells and used to produce the Nla III endonuclease and methylase on a large scale and in substantially pure form, for commercial purposes.

In accordance with the present invention, recombinant DNA encoding the Nla III endonuclease and methylase are obtained using a modified version of the vector modification approach described in EPO Publication No.0193413. It has been found in accordance with the present invention that the Nla III R-M system is genetically more complex than previously isolated type II R-M systems such as those described in the above-referenced EPO publication. Although the Nla III endonuclease and methylase genes were ultimately found to be linked, the endonuclease gene was not intact in any of the clones obtained using vector modification.

From restriction mapping studies, the Nla III methylase gene was located in a region of approximately 1300 base pair on the *N. lactamica* genome. Upstream (5') of this region, all of the methylase clones terminated within approximately 415 base pair of the Nla III methylase gene region.

In contrast, the clones contained variable lengths of DNA which extended downstream (3') of the methylase gene by as much as 3700 base pair. It was believed, therefore, that if the genes were linked, the Nla III endonuclease gene was located upstream (5') of the methylase gene. L. The abrupt truncation of all the Nla III methylase clones in the upstream region of the genome was a phenomenon which had not previously been observed in cloning of type II R-M systems. Several explanations for this phenomenon were possible. The Nla III endonuclease and methylase genes could have been unlinked. Alternatively, introduction of both genes into a host cell simultaneously could have been a lethal event.

For unknown reasons, the Nla III endonuclease gene could not be cloned intact from clones carrying the Nla III methylase gene. It was therefore necessary to clone pieces of the endonuclease gene and to use recombinant technology to reconstruct the gene.

Based on the assumption that the endonuclease gene was linked to the methylase gene, the DNA upstream from the Nla III methylase gene was sequenced. A 520 base pair open reading frame was found which was contiguous to the Nla III methylase gene.

A map of restriction sites in *N. lactamica* genomic DNA was produced by Southern blotting, using as probes the Nla III methylase clones and synthetic oligonucleotides complementary to the portion of the 520 base pair open reading frame corresponding to the presumed carboxyl-terminus of the endonuclease. Restriction fragments were identified which hybridized to the probes and contained enough DNA to encode the presumed endonuclease gene.

The DNA corresponding to the amino terminal portion of the presumed endonuclease gene was isolated in sufficient quantities to be subcloned into a separate vector. The two parts of the presumed endonuclease gene were then joined and cloned into host cells into which the Nla III methylase gene had previously been introduced.

Subsequently, it was found that this pre-modification approach, while successful, was not strictly required. The Nla III endonuclease gene can be introduced to unmodified host cells at low frequency when a second compatible plasmid which contains only Nla III methylase is co-transformed with a plasmid containing both Nla III R-M genes.

The preferred method for cloning recombinant DNA containing the Nla III restriction endonuclease and modification methylase genes is set forth below, and is represented in FIG. 1.

A. Cloning of Nla III Methylase Gene

The genomic DNA of *N. lactamica* is purified using known methods and partially digested with an appropriate restriction endonuclease. The preferred restriction endonuclease for forming the genomic library is HinP I. The digested genomic DNA is then ligated to a cloning vector containing one or more Nla III, BspH I, or Sph I recognition sites, all of which contain the recognition sequence of Nla III. The latter two, BspH I and HinP I, are subsets of the Nla III recognition sequence and are blocked by Nla III methylation. In theory, Nco I could be used for selection, as it is also a subset of Nla III. It was found, however, that NcoI is insensitive to Nla III methylase and thus cannot be used for selection of Nla III clones. The preferred cloning vector is pUC19; however, other cloning vectors may also be used as long as they contain Nla III, BspH I, or Sph I sites. Such vectors include pBR322 and derivatives, pACYC177 or 184, and the like. The ligated DNA is then transformed into an appropriate bacterial host such as *E. coli* RR1 (ATCC 31343) or *E. coli* ER1398. Other bacterial hosts which do not restrict the *N. lactamica* DNA or otherwise interfere with cloning of the methylase gene may also be used. Transformants are selected by plating onto a medium containing an antibiotic or other selection pressure. When pUC19 is used as the cloning vector, for example, the transformants are plated onto Luria agar containing ampicillin.

Recombinant plasmids should be ampicillin resistant and carry inserts of *N. lactamica* genomic DNA. The ampicillin-resistant colonies are pooled to form the primary cell library. From this pool, recombinant plasmids are purified away from the transformation host's genomic DNA by known methods such as density centrifugation with CsCl and ethidium bromide. The purified recombinant plasmids form the primary plasmid library.

The primary plasmid library is then digested to completion with a suitable endonuclease such as Nla III, BspH I, or Sph I. The Nla III recognition site (CATG) is contained within the BspH I site (TCATGA) and within the Sph I site (GCATGC). It was found in accordance with the present invention that methylation by the Nla III methylase also protects DNA from BspH I and Sph I endonuclease digestion.

Thus, digestion by Nla III, BspH I, or Sph I endonucleases differentially destroys DNA which has not been modified by the Nla III methylase, increasing the proportion of plasmids containing the Nla III methylase gene in the primary plasmid library.

The Nla III methylase gene-enriched plasmid library is then transformed back into an appropriate bacterial host such as *E. coli* RR1. Transformants are recovered by plating onto a selective medium such as L-agar containing ampicillin. The DNA of surviving colonies is analyzed for the presence of the Nla III methylase gene, by digestion with the Nla III, BspH I, and/or Sph I endonucleases. This analysis is performed both on purified plasmid DNA and on total cellular (genomic and plasmid) DNA. Clones carrying the Nla III modification gene contain fully modified NlaIII sites, and both plasmid and genomic DNA is substantially resistant to digestion by Nla III, BspH I, and Sph I endonucleases.

B. Restriction Mapping of *N. lactamica* Genomic DNA

In the absence of genetic complexities inherent to certain type II R-M systems, if the methylase and endonuclease genes are linked, selection for methylase genes should also yield clones carrying the endonuclease gene. As noted above, however, the Nla III R-M system was more complex, and none of the Nla III methylase+ clones yielded intact endonuclease genes. In order to determine whether the Nla III methylase and endonuclease genes are linked and where the Nla III endonuclease gene is located in relation to the Nla III methylase gene, it is necessary to create a restriction map of the *N. lactamica* genome in the region of the methylase.

The Nla III methylase clones are themselves used to perform Southern blotting restriction mapping studies. The methylase clones are also used to localize the methylase gene, since the methylase gene will be located in the least DNA common to all methylase positive clones. The methylase clones are then sequenced to determine the precise location and orientation of the methylase gene, to identify the open reading frame presumed to be the endonuclease, and to guide the synthesis of oligonucleotide primers exactly complementary to the *N. lactamica* DNA in the presumed endonuclease gene or methylase gene. A restriction map of *N. lactamica* DNA upstream (5') of the methylase gene is created by digesting *N. lactamica* DNA with various restriction endonucleases such as Rsa I, Mbo I, Cla I, HinP I, BssH II, Hinc II, etc., and performing Southern blotting using the methylase clones or synthetic oligomers as probes.

C. Isolation and Identification of Nla III Endonuclease Gene

Host cells which are pre-modified with the Nla III methylase are prepared by transferring the Nla III methylase gene to a vector, such as pACYC184 (ATCC 30733) along with a second vector which can replicate in the same cell such as pUC19 because these vectors employ different origins of the replication. The methylase containing-pACYC184 vector is transformed into *E. coli* RRI and selected for methylase clones as above. Methylase containing cells produced in this manner have the Nla III sequences in their DNA modified prior to the introduction of Nla III endonuclease, which increases their chance for survival when the endonuclease is cloned into the cells on the second vector.

*N. lactamica* genomic DNA is digested with a restriction enzyme, preferably Rsa I, to produce a DNA fragment containing the complete endonuclease gene, or at least the amino-terminal portion missing from the methylase clones. Rsa I digests yield a 2.0 kb fragment containing the entire R-M genes.

The Rsa I fragment is ligated at low concentration to circularize the DNA. Oligonucleotide primers complementary to this Nla DNA fragment are hybridized to the circularized DNA, and the concentration of DNA encoding the restriction endonuclease gene is increased using gene amplification techniques such as the polymerase chain reaction (PCR). Amplification greatly increases the frequency of DNA encoding the Nla III endonuclease or a portion thereof and thus the identification of such clones as described below.

The amplified DNA is digested with a restriction enzyme, preferably Sau3A I, to produce a fragment containing the portion of the endonuclease gene missing from the methylase clones obtained by the standard cloning method. This fragment is cloned into a vector such as pUC19 (ATCC #37254). Sau3A I is used because the approximately 500 base pair fragment produced contains the amino terminal portion of the endonuclease gene and overlaps the previously cloned portion of the endonuclease gene by 178 base pair. Also, Sau3A I does not cleave the *N. lactamica* genomic DNA used for the PCR reaction and thus only amplified (the desired) DNA is cleaved and made available for ligation.

Clones containing the missing amino-terminal portion of the endonuclease are identified by restriction mapping the cloned DNA and comparing the restriction map of genomic *N. lactamica* DNA produced by Southern blotting and from the methylase clones.

The complete endonuclease gene is obtained by: a) cleaving a clone containing the methylase and carboxyl-terminal portion of the endonuclease gene with an enzyme that cleaves in the endonuclease at a single site, such as Cla I, and an enzyme that cleaves in the vector, such as Pst I; b) cleaving a clone that contains the amino-terminal portion of the endonuclease gene with the same enzyme, Cla I, as used on the carboxyl-terminal clone and the same enzyme, Pst I, used to cleave outside the endonuclease gene in the vector; c) gel purifying the fragments containing the two parts of the endonuclease gene (one fragment of which also contains the cloning vector); d) ligating the two gel-purified fragments together to form an intact endonuclease gene in a vector containing the methylase gene; e) introducing the ligated vector containing the intact endonuclease and methylase genes into a cell, such as *E. coli* RRI, pre-modified with the Nla III methylase contained on a compatible vector system, such as the plasmid pACYC184; and f) identifying clones expressing the Nla III endonuclease by preparing cell extracts of those clones found to contain both fragments of the endonuclease gene as determined by restriction mapping.

D. Production of Recombinant Nla III Endonuclease and Methylase

Recombinant Nla III restriction endonuclease and methylase may be produced from clones carrying the Nla III restriction and modification genes by propagation in a fermenter in a rich medium containing ampicillin. The cells are collected by centrifugation and disrupted by sonication to produce a crude cell extract containing the Nla III restriction endonuclease activity.

The crude cell extract containing the Nla III restriction endonuclease and/or methylase activity is purified by standard protein purification techniques such as affinity-chromatography and ion-exchange chromatography. Recombinant endonuclease so produced is free of other contaminating enzymes including Nla I, Nla II and Nla IV, and substantially free of non-specific nucleases.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Nla III Restriction Endonuclease Gene

1. DNA purification: 5 g of frozen *Neisseria lactamica* (NRCC 2118) cells were resuspended in 20 ml of 25% sucrose, 50 mM Tris pH 8.0. 10 ml of 0.25M EDTA pH 8.0, and 6 ml of 10 mg/ml lysozyme in 0.25M Tris pH 8.0 were added. The suspension was kept on ice for 16 hours, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 60 ml of chloroform. The emulsion was centrifuged at 10K rpm for 30 minutes to separate the phases. The viscous upper phase was dialyzed against four changes of DNA buffer (10 mM Tris pH 8.0, 1 mM EDTA). The dialyzed solution was then digested with RNase at a final concentration of 100 $\mu$g/ml for 2 hours at 37° C. The DNA was then precipitated by the addition of 5M NaCl to a final concentration of 0.4M, and 0.55 volumes of isopropyl alcohol. The precipitated DNA was spooled onto a glass rod, air-dried, then dissolved in DNA buffer to a concentration of approximately 350 $\mu$g/ml and stored at 4° C.

2. Digestion of DNA: 50 $\mu$g of *N. lactamica* DNA was diluted into 500 $\mu$l of HinP I restriction endonuclease digestion buffer (10 mM Tris pH 8.0, 10 mM MgCl$_2$, 50 mM NaCl). A serial dilution of HinP I restriction endonuclease from 4 units/$\mu$g to 0.06 units/$\mu$g was performed and the solutions were incubated at 36° C. for 1 hr. The extent of HinP I digestion was analyzed by gel electrophoresis of a small aliquot from each dilution. The dilutions which produced a range of fragments of the desired size (2Kb–15Kb) were then pooled and extracted with an equal volume of equilibrated phenol, followed by two extractions with chloroform. The DNA was precipitated by the addition of 5M NaCl to a final concentration of 0.4M and 0.55 volumes of isopropyl alcohol. The DNA was then dissolved in DNA buffer to a concentration of approximately 100 $\mu$g/ml.

3. Ligation and transformation: 6 $\mu$g (60 $\mu$l) of HinP I-digested *N. lactamica* DNA was mixed with 3 $\mu$g (15 $\mu$l) of Acc I-cleaved and dephosphorylated pUC19 (ATCC 37254). 20 $\mu$l of 10× ligation buffer (500 mM Tris pH 7.5, 100 mM MgCl$_2$, 100 mM DTT, 5 mM ATP), and 105 $\mu$l of sterile distilled water (dH$_2$O) were added to bring the volume to 200 $\mu$l. 7.5 $\mu$l (3000 NEB units) of T4 DNA ligase was added and the solution was incubated at 17° C. for 16 hours. The solution was sterilized by extraction with 20 $\mu$l of chloroform, then clarified by microcentifugation for 15 seconds. 62.5 $\mu$l of the ligation solution was mixed with 500 $\mu$l of SSC/CaCl$_2$ (50 mM NaCl, 5 mM Na$_3$Citrate, 67 mM CaCl$_2$ and 1.0 ml of ice-cold, competent *E. coli* RR1 (ATCC 31343) cells were added. The solution was incubated at 42° C. for 4 minutes, then 10 ml of Luria-broth (L-broth) was added and incubation was continued at 37° C. for 3 hr.

4. Cell Library: The transformed culture was gently centrifuged, the supernatant was discarded and the cells were resuspended in 1.0 ml of L-broth. 200 $\mu$l portions of the resuspended cells were plated onto Luria-agar (L-agar) plates containing 100 $\mu$g/ml ampicillin. The plates were incubated overnight at 37° C. The transformed cells that grew up on the surfaces of the plates were collected together by flooding each of the plates with 2.5 ml of 10 mM Tris pH 7.5, 10 mM MgCl$_2$, scraping the colonies together, and pooling the suspensions into a single tube.

5. Plasmid Library: 2.0 ml of the cell library was inoculated into 500 ml of L-borth containing 100 $\mu$g/ml ampicillin. The culture was shaken overnight at 37° C. then centrifuged at 5K rpm for 5 minutes. The supernatant was discarded and the cell pellet was resuspended in 10 ml of 25% sucrose, 50 mM Tris pH 8.0, at room temperature. 5ml of 0.25M EDTA, pH 8.0,and 3 ml of 10 mg/ml lysozyme in 0.25M Tris pH 8.0 were added. The solution was kept on ice for 1 hour, then 12 ml of 1% Triton X-100, 50 mM Tris pH 8.0, 67 mM EDTA was added and the suspension was gently swirled to induce cell lysis.

The lysed mixture was transferred to a 50 ml tube and centrifuged for 45 minutes at 17K rpm, 4° C. The supernatant was removed with a pipette. 20.0 gm of solid CsCl was weighed into a 50 ml plastic screw-cap tube and 22.0 gm of supernatant was pipetted into the tube and mixed. 0.5 ml of 10 mg/ml ethidium bromide in 10 mM Tris pH 8.0, 100 mM NaCl, 1 mM EDTA was added. The solution was transferred to two ⅜ in.×3 in. centrifuge tubes and spun in a Beckman Ti70 rotor for 30 hours at 50K rpm, 17° C. To collect the plasmids, the tubes were opened, illuminated with ultraviolet light, and the lower of the two fluorescent bands was collected by syringe. The lower band from each tube was combined and the ethidium bromide was removed by extracting three times with an equal volume of water-saturated, $CsCl_2$ saturated isopropyl alcohol.

The extracted solution was diluted with four volumes of DNA buffer, then the nucleic acid was precipitated by the addition of 2 volumes of isopropanol. The solution was placed at $-70°$ C. for 30 minutes then centrifuged for 15 minutes at 15K rpm, 4° C. The supernatant was discarded, the pellet was air-dried for 30 minutes then dissolved in 1 ml of 10 mM Tris pH 8.0, 1 mM EDTA and stored at 4° C. The plasmid DNA concentration was found to be approximately 200 μg/ml.

6. Digestion of the Plasmid Library: 4 μg (20 μl) of the plasmid library was diluted into 100 μl of BspH I restriction endonuclease digestion buffer (10 mM Tris pH 7.4, 10 mM $MgCl_2$, 100 mM KCl. 16 units (4 μl) of BspH I restriction endonuclease and 8 units (2 μl) of Sph I restriction endonuclease were added and the tube was incubated at 37° C. for 2 hours. The reaction was sterilized by extraction with 20 μl chloroform, then clarified by microcentrifugation for 15 seconds.

7. Transformation: 20 μl (0.8 μg) of the digested library was mixed with 100 μl of $SSC/CaCl_2$ (section 3) and 200 μl of ice-cold, competent, E. coli RR1. The mixture was warmed to 42° C. for 3 minutes and then plated onto an L-agar containing 100 μg/mg ampicillin. The plate was incubated overnight at 37° C. BspH I and Sph I digestion reduced the number of transformants $10^3$-fold compared with transformation by undigested plasmids. Approximately two hundred colonies grew following the BspH I and Sph I digestion; seventy were inoculated into 10 ml of L-broth containing ampicillin, to prepare miniculture, and streaked onto an L-agar plate containing ampicillin, to prepare a master stock.

8. Analysis of surviving individuals: Seventy of the surviving colonies obtained from section 7 were grown into 10 ml cultures and the plasmids that they carried were prepared by the following miniprep purification procedure, adapted from the method of Birnboim and Doly, Nucleic Acids Res. 7: 1513 (1979).

Miniprep Procedure: Each culture was centrifuged at 8K rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were gently shaken to lyse the cells, then placed on ice. Once the solutions had cleared, 1.5 ml of 3M sodium acetate, pH 4.8, was added to each and shaken. The precipitates that formed were spun down at 15K rpm, 4° C. for 10 minutes. Each supernatant was poured into a centrifuge tube containing 3 ml of 2-propanol and mixed. After 10 minutes at room temperature, the tubes were spun at 15K rpm for 10 minutes to pellet the precipitated nucleic acids. The supernatants were discarded and the pellets were air-dried at room temperature for 30 minutes. Once dry, the pellets were then dissolved in 500 μl of 10 mM Tris, 1 mM EDTA, pH 8.0, containing 100 μg/ml RNase and incubated for 1 hour at 37° C. to digest the RNA. The solution was transferred to a 1.5 ml Eppendorf tube and the DNA was precipitated once more by the addition of 50 μl of 5M NaCl followed by 350 μl of 2-propanol. After 10 minutes at room temperature, the DNA was spun down by centrifugation for 5 minutes and the supernatants discarded. The pellets were air-dried at room temperature for 30 minutes, then redissolved in 150 μl of 10 mM Tris 1 mM EDTA, pH 8.0. The plasmid minipreps were subsequently analyzed by digestion with BspH I, Sph I and/or Nla III, and HinP I.

9. Nla III Methylase Gene Clones: Sixty-one of the seventy plasmids that were analyzed were found to be sensitive to BspH I digestion and to carry diverse HinP I fragments of N. lactamica DNA. These plasmids were spurious and were discarded. The remaining 9 plasmids were found to be resistant to BspH I, Sph I and to Nla III digestion and to carry a 0.59 Kb and a 0.54 Kb HinP I fragment in common. Six different plasmid constructs were obtained and found to fully protect the plasmids from BspH I, Sph I and Nla III digestion. Methylase clones were also obtained from Mbo I, EcoR I and Cla I libraries through the same methylase selection techniques. None of these clones contained any detectable Nla III endonuclease activity 10. Sequencing the Nla III methylase clones: The Nla III methylase clones were sequenced using the Sanger dideoxy chain termination method. The ends of the cloned pieces of DNA were sequenced using the universal primers NEB #1201 and #1211, which hybridize to the pUC19 vector near the cloning site and read into the cloned DNA. In a typical reaction, 2 μg (2 μl) phenol/chloroform extracted miniprep plasmid DNA was diluted to a total volume of 20 μl with dH2O. 2 μl of 2M NaOH, 2 mM EDTA was added and the solution was incubated at room temperature for 5 minutes. In rapid succession was added 7 μl dH2O, 6 μl 3M NaAcetate (pH 6.0) and 75 μl ethanol. The DNA was precipitated 15 minutes in a 2-propanol/dry ice bath, pelleted by centrifugation 10 minutes in an eppendorf centrifuge, washed with 200 μl 70% ethanol/ 30% dH2O, recollected by centrifugation and dried. The DNA was then resuspended in 9 μl dH2O, 1.5 μl 10×sequencing buffer (100 mM Tris-HCl pH 7.5, 50 mM $MgCl_2$, 75 mM DTT) and 1 μl (1 pmole) of a 1 uM primer solution The reaction was incubated 30 minutes at 37° C. 2 μl of [alpha-35S]dATP (500 Ci/mmole, 10 mCi/ml) and 1 μl (5 u) Klenow fragment were added, the solution mixed and 3.2 μl were dispensed into each of the A,C,G and T reaction tubes which contained 3.0 μl of the appropriate NEB #406 didoexy sequencing reagents The reactions were incubated 15 minutes at 37° C., then 1 μl dNTP chase solution (NEB #406) was added and incubation continued for an additional 15 minutes. 6 μl stop solution was added and the reactions were electrophoresed on an 8% bis-acrylamide sequencing gel, followed by autoradiography.

Subclones of the methylase were created to bring interior portions of the clone close to the pUC19 universal priming sites so that sequences could be determined. These subclones were formed as follows. Two micrograms of the HinP I library methylase clone pRM125M 122-64 obtained as described in steps 1-9 was digested with 20 u EcoR I and 20u Pst I in a 50 μl reaction for 1 hour, then electrophoresed on a 1% FMC Sea-Plaque(rt) LMP agarose gel in 40 mM Tris-HCl pH 8.0, 20 mM NaAcetate, 1 mM Na$_2$EDTA, 0.5 μg/ml ethidium bromide. The 1.7 kb fragment of cloned DNA was cut out of the gel. 5 μl of the gel fragment was mixed with 1 μl 10×reaction buffer, 4 μl dH2O, and 1 μl (5 u) HinP I and digested for 30 minutes at 37° C. The reaction was heated to 65° C. for 15 minutes, then extracted with 10 μl chloroform. 1.3 μl 10×ligation buffer was added, along with 1 μl T4 DNA ligase and 1 μl (200 ng) Acc I cleaved and dephosphorylated pUC19 DNA and the solution was incubated for 16 hrs at 4° C. The ligation product was melted at 65° C. for 5 minutes and cooled to 42° C. 5 μl of the melted ligation product was mixed with 100 μl ice-cold competent E. coli RRI cells, heated to 42° C. for 4 minutes and plated on LB agar containing 100 μg/ml ampicillin. Subclones obtained in this manner were sequenced as above using the NEB #1201 and #1211 universal primers. Further sequencing was performed by synthesizing primers complementary to the N. lactamica DNA as above to complete the sequence.

11. Construction of a restriction map of N. lactamica genomic DNA by Southern blotting: Genomic N. lactamica DNA was diluted into endonuclease reaction buffer at a concentration of 50 mg/ml and cleaved with various restriction endonucleases, including Ban II, BssH II, BstB I, Cla I, EcoR V, Hinc II, HinP I, Mbo I, Rsa I, and Pst I. 2 μg of the digested DNA was electrophoresed in a 1% LE agarose gel in 40 mM Tris pH 8.0, 20 mM NaAcetate, 1 mM Na2EDTA, 0.5 μg/ml ethidium bromide. The gel was photographed under UV illumination along with a ruler to determine migration distances, then soaked in 250 ml of 0.25M HCl with gentle agitation for 15 minutes. The gel was then drained and soaked in a second aliquot of 250 ml of 0.25M HCl for an additional 15 minutes. The gel was rinsed and placed in 250 mls of 0.5M NaOH, 1.5M NaCl with gentle agitation for 15 minutes, the buffer was replaced and a second 15 minute soak performed. The gel was then rinsed and placed in 250 mls of 1M NH$_4$OAc, 0.02M NaOH for 30 minutes with gentle agitation, following which the NH$_4$OAc/NaOH buffer was changed and a second 30 minute soak performed. The DNA was then transferred overnight to a sheet of Schleicher & Schuell Ba85 nitrocellulose (pre-wet in the NH$_4$OAc/NaOH buffer) by capillary action. The nitrocellulose blot was then baked in a vacuum oven at 80° C. for 2 hours. The blot was probed with nick-translated methylase clone, prepared by combining library, pRM125M1-15, with 4 μl 0.1 mM dATP,4 μl 0.1 mM dGTP, 4 μl 0.1 mM dTTP, 10 μl 800 Ci/mmole, 10 mCi/ml [alpha-32P] dCTP, 4 μl 0.1 μg/ml DNase I and 1 μl (10 units NEB) E. coli DNA polymerase I in 100 μl total volume of 50 mM Tris-HCl pH 7.8, 5 mM MgCl$_2$, 10 mM 2-mercaptoethanol and 50 μg/ml bovine serum albumin. The solution was incubated for 3 hours at 15° C., then 5 μl of 250 mM dATP, dCTP, dGTP, dTTP was added and incubated for an additional 15 minutes. The DNase and DNA polymerase were inactivated by heating the solution to 98° C. for 5 minutes. The nitrocellulose blots were placed in a sealed bag with 15 mls of hybridization solution (10×Denhardts's solution, 6×SSC, 1% SDS, 2% Dextran sulfate)) for 2 hours. 50 μl of the nick-translated plasmid was then added and allowed to hybridize for 16 hours at 65° C. The hybridization solution was then removed and the filter was washed 3 times for 5 minutes each time in 250 ml of 2×SSC at 65° C., followed by three washes for 20 minutes each with 250 ml of 2×SSC, 0.5% SDS at 65° C. The filter was then rinsed in dH2O and an autoradiogram was produced indicating the size of the various restriction fragments.

12. Transferring the Nla III methylase to pACYC184: Four micrograms of Nla III methylase clone pRM125M 122-64 was digested with 10 u Pvu II in a volume of 100 μl. Ten micrograms of pACYC184 was digested with 40 units of Pvu II in a total reaction volume of 200 μl. The cleaved pACYC184 DNA was extracted once with equilibrated phenol and then twice with chloroform, the NaCl concentration was brought to 100 mM, 2 volumes of ethanol were added and the solution incubated at −70° C. for 30 minutes to precipitate the DNA. The precipitated DNA was collected by centrifugation, washed with 300 μl of 70 % ethanol/30% dH2O, recollected by centrifugation, dried, and resuspended in 43 μl of 10 mM Tris-Hcl pH 8.0, 1 mM Na$_2$EDTA.

The Pvu II digested pACYC184 was treated with calf intestinal phosphatase (CIP) to prevent ligation of the vector to itself. 5 μl of 10×CIP buffer (500 mM Tris-HCl pH 9.0, 10 mM MgCl$_2$, 1 mM ZnCl$_2$) was added to the 43 μl of pACYC184. 1 μl (1 u) of CIP was added and the reaction was incubated at 37° C. for 15 minutes, then 56° C. for 15 minutes. A second 1 μl (1 u aliquot) of CIP was added and again incubated for 15 minutes at 37° C., then 56° C. for 15 minutes. The reaction was extracted with phenol and chloroform and precipitated as above. The dried DNA was resuspended to a concentration of approximately 200 μg/ml. 1 μg of Pvu II digested pRM125M 122-64 was combined with 0.5 μg dephosphorylated Pvu II cleaved pACYC184 in a volume of 25 μl of ligation buffer, to which 3 μl (300 NEB units) of T4 DNA ligase was added, followed by incubation at 17° C. for 16 hours. 5 μl of the ligated DNA was then mixed with 200 μl ice-cold competent E. coli RRI cells and warmed to 42° C. for 4 minutes. 10 ml of Luria broth was added and the cells incubated for 3 hours at 37° C. The cells were then collected by gentle centrifugation and plated on LB agar containing 50 μg/ml tetracycline. The resulting colonies were screened for the presence of Nla III methylase activity. Competent cells were prepared from pACYC184 Nla III methylase transformants.

13. Amplification of the missing portion of the endonuclease gene: Using the mapping information generated from Southern blots of N. lactamica genomic DNA, Rsa I and BssH II were chosen to cleave N. lactamica DNA for inverse PCR amplification. 10 μg of N. lactamica DNA were cleaved in a 100 μl reaction with 20 u of BssH II or 40 u of Rsa I. Fragments in the size range of 2000 base pairs for Rsa I and 4500 base pairs for BssH II were gel purified as in step 10 above. The agarose containing the gel purified DNA fragments was melted at 65° C., cooled to 42° C. and diluted to 1 ml with 1×T4 DNA ligase buffer to achieve a concentration of approximately 1 μg/ml, a concentration low enough to favor the circularization of the DNA fragments in the ligation process. 20 μl (10,000 NEB units) of T4 DNA ligase was added and the reaction was incubated at 17° C. for 16 hours. The ligation reactions were then extracted with an equal volume of equilibrated phenol, followed by two extractions with chloroform, brought to 100 mM NaCl, divided into two Eppendorf tubes and precipitated with two volumes of ethanol at −70° C. for 16 hours. The precipitated DNA was collected by centrifugation, washed with 300 μl of 70% ethanol/30% dH2O, centrifuged and dried.

PCR amplification was performed on the ligated DNA fragments as follows. To one tube containing the 500 ng ligated, purified and dried Rsa I fragments (approximately 500 ng DNA) was added 100 μl of 140 mM Tris-HCl pH 8.4, 40 μl of 1 mM dNTP solution, 2 μl 200 mM MgCl2, 2 μl of 10% Triton-X 100, 15 μl (500 nmolar final concentration) primer Nla III #4 (5' GATCGTATTGATAACATCCG 3') and 23 μl dH2O. The reaction was mixed and divided as follows. To 20 μl of the mix was added 2 μl of primer Nla III #9 (5' GCAATTCTATAGATGCAATCCGCCT-TAATGG 3') (to 500 nmolar), 0.25 μl (0.6 u) Taq I polymerase and 1 μl of 2 mg/ml bovine serum albumin (BSA). This reaction was a control for the presence of the Rsa I fragment containing the Nla III endonuclease gene and did not require the Rsa I fragment to have been circularized for amplification to occur. To the remaining 162 μl was added 13 μl of primer Nla III (5' CAAATATACATCGGACTAC 3') #7 (to 500 nmolar), 8 μl of BSA and 2 μl (5u) of Taq I polymerase. The reaction was split in half and 1.8 μl of 200 mM MgCl2 was added to one of the tubes. 50 μl of parafin oil was layered over the reactions, which were incubated for 25 cycles consisting of; 93° C. for 1.5 minutes, 44° C. for 1.2 minutes and 70° C. for 8.5 minutes. Samples of 16 μl were then removed, mixed with 6 μl stop dye and analyzed by electrophoresis in a standard 1% agarose gel. The same experiment was performed with the BssH II ligated, purified and dried DNA. The Rsa I 2 mM MgCl2 reaction with primers #4 and #7 produced approximately 3 μg of DNA at the expected size of 2000 base pairs. Similar reactions with the BssH II digested and ligated DNA did not produce any amplified DNA, although the BssH II control experiment did produce the expected fragment of approximately 1200 base pairs. The amplified DNA obtained from the Rsa I amplification was extracted with phenol and chloroform and precipitated as above.

14. Cloning from amplified DNA:-Sau3A I was used to clone the amino-terminal portion of the endonuclease gene from the amplified DNA. Sau 3AI was chosen because a single 500 base pair Sau 3AI fragment was suspected to contain the missing portion of Nla III endonuclease, and because *N. lactamica* genomic DNA is methylated such that Sau3A I will not cleave, so that only the amplified DNA and not the starting genomic DNA would be cleaved and available for ligation into the vector. 5 μl of amplified DNA (0.3 μg) was diluted into 25 μl Sau3A I reaction buffer, 1 μl (5 u)-Sau3A I was added and incubated for 1 hour at 37° C. The reaction was then extracted with phenol and chloroform and precipitated as above. The precipitated DNA was resuspended in 17 μl dH2O, to which was added 2 μl of 10× ligation buffer, 1 μl (100ng) of BamH I cleaved and dephosphorylated pUC19 DNA and 1 μl (100u NEB) of T4 DNA ligase. The reaction was incubated at 17° C. for 16 hours, then extracted with 10 μl chloroform. 10 μl of the ligation reaction was mixed with 200 μl ice-cold competent *E. coli* RRI dam- cells (GM 2971 dam13::tn9), warmed to 42° C. for 4 minutes and plated on LB-agar plates containing 100 μg/ml ampicillin. Individual amp-resistant colonies were picked, minipreped, and their plasmid DNA analyzed by restriction mapping for the presence of a 500 base pair Sau3A I fragment containing 178 base pairs of previously cloned an sequenced DNA and approximately 325 base pairs of DNA believed to encode the missing portion of the endonuclease gene. Out of 14 minipreps analyzed, one such clone, pRM125amp 113-11 was obtained.

15. Creating the intact Nla III endonuclease gene: 2 μg of the EcoR I library methylase clone pRM125M 101-8 was digested with 20 u BamH I in a 50 μl reaction for 1 hour at 37° C. The 7.4 kb fragment, which includes the methylase and entire pUC19 vector (except the polylinker from the EcoR I site to the BamH I site, bases 396 to 417) was gel purified from a 1% LMP agarose gel, ligated and transformed into *E. coli* RRI dam- cells (as above, section 10). This BamH I deletion eliminated a second Cla I site from the clone. Growing the plasmid in a dam minus host made the Cla I site in the endonuclease gene cleavable, because the overlapping Mbo I site was no longer methylated by the *E. coli* dam methylase. The BamH I deleted plasmid, pRM125M 101-8dBamH was miniprepped and 8 μl (appx. 4 μg) of this DNA was diluted into 50 μl Cla I reaction buffer. 1 μl (6u) Cla I, 1 μl (20 u) Pst I and 1 μl (15 u) EcoO 109 I were added and the reaction incubated for 2 hrs at 37° C. EcoO 109 I was used to facilitate the gel purification of the desired fragment by cleaving a similar size unwanted fragment into two smaller fragments. Cla I cleaves in the area of overlap between the two portions of the endonuclease gene which were cloned separately and is the site where the two parts of the endonuclease gene are joined. Pst I occurs in the vector only and is used to join the end of the cloned fragment outside the methylase and endonuclese genes to the vector. 10 μl (2 μg) of pRM125amp 113-11, the Sau3A I fragment clones from the the amplification process, was diluted into 50 μl Cla I reaction buffer and 1 μl (6 u) of Cla I and 1 μl (20 u) of Pst I were added, and the reaction was incubated at 37° C. for 2 hours. The 2.9 kb Cla I to Pst I fragment from pRM125M 101-8dBamH and the 3.2 kb Cla I to Pst I fragment (including the pUC19 vector) from pRM125amp 113-11 were gel purified from 1% LMp agarose as above. The gel slices were melted at 65° C. for 5 minutes and 10 μl (appx. 200 ng) of the 2.9 kb pRM125M 101-8dBamH fragment was mixed with 3 μl (appx. 60 ng) of the 3.2 kb pRM125amp 113-11 fragment. The mixture was cooled to 42° C. and 13 μl of 2×T4 DNA ligase buffer containing 0.5 μl (50 u NEB) T4 DNA ligase was added, mixed and the reaction incubated at 17° C. for 16 hours. The ligation reaction was then melted at 65° C. for 5 minutes and cooled to 42° C. 10 μl of the ligation product was mixed with 200 μl of ice-cold competent *E. coli* RRI cells carrying the pACYC184-Nla III methylase plasmid pRM125M ACYC-4, incubated at 42° C. for 4 minutes and then plated on LB agar plates containing 100 μg/ml ampicillin and incubated at 30° C. for 24 hours. The 8 colonies which grew were miniprepped, their plasmid DNA was analyzed by digestion with EcoR I, and 7 of the 8 were found to contain the intended construct. These plasmids were named pRM125RM 100c-1 through 8.

16. Nla III Restriction Gene Clone: pRM125RM 100c-4 (a sample of which was deposited with the American Type Culture Collection on Jul. 17, 1990 under ATCC designation No. 68366 in *E. coli* ER1398) and similar plasmids, were found to encode and express the Nla III restriction endonuclease by assaying extracts of *E. coli* RR1 that carried the plasmids. pRM125RM 100c-4 also contains the DNA encoding the Nla III methylase.

Endonuclease Assay

A 250 ml culture of the cells to be assayed was grown overnight at 37° C. in L-broth containing 100 μg/ml ampicillin. The culture was centrifuged at 8K rpm for 5 minutes and the cell pellet was resuspended in 10 ml of 10 mM Tris-HCl pH 7.5, 10 mM 2-mercaptoethanol, 1 mM MgCl$_2$. 1.5 ml of the suspension was sonicated for three 15-second bursts to disrupt the cells. The sonicated extract was microcentrifuged for 10 min to remove cell debris and the supernatant was assayed for endonuclease activity in the following way:

8 μg (16 μl) of purified phage lambda DNA was diluted into 400 μl of Nla III restriction endonuclease digestion buffer (section 6). The solution was dispensed into 7 tubes, 75 μl into the first tube and 50 μl into each of the remaining 6 tubes. 13.5 μl of the extract was added to the first tube to achieve 9 μl extract/μg DNA. 25 μl was then removed from the first tube and transferred to the second tube to achieve 3 μl/μg. 25 μl serial transfers were continued into tubes 3 (1 μl/μg), 4 (0.3 μl/μg), 5 (0.1 μl/μg), 6 (0.03 μl/μg) and 7 (0.01 μl/μg). The tubes were incubated at 37° C. for one hour, then 20 μl from each was analyzed by gel electrophoresis. The extract was found to contain approximately $2 \times 10^3$ units of Nla III restriction endonuclease per ml, which corresponds to $2 \times 10^4$ units per gram of cells.

17. *E. coli* ER1398 carrying pRM125RM 100c-4 is the preferred host from which the Nla III restriction endonuclease can be purified. Other host cells which can be used include *E. coli* RR1, *E. coli* MM294, and the like. The strain should be grown to late log phase at 37° C. in a fermenter, in L-broth containing ampicillin. The cells should then be collected by centrifugation and either broken immediately for exact preparation, or stored frozen at −70° C. until it is convenient to do so.

18. Purification of recombinant NlaIII endonuclease: 25 grams of *E. coli* ER1398 cells carrying plasmid pRM125RM 100c-4 were resuspended in 100 ml buffer A (20 mM KP04 pH7.0 10 mM 2-mercaptoethanol, 0.1 mM EDTA). The cells were disrupted by sonication. The release of soluble protein was monitored and sonication continued until 6% of the starting cell paste weight was released as soluble protein. 5M NaCl was added to bring the total NaCl concentration to 0.1M and the solution was clarified by centrifugation for 30 minutes at 12,000 rpm at 4° C. with a Beckman J2-21 centrifuge and JA-14 head. The crude supernatant was then applied to a 2.5×11 cm Phosphocellulose column equilibrated with buffer B (buffer A containing 0.1M NaCl). The column was washed with 100 ml of buffer B. A 600 ml linear gradient from 0.1 NaCl to 1.1M NaCl in buffer A was applied to the column and 10 ml fractions were collected. The peak of Nla III activity was determined by assaying the column fractions with lambda DNA as above. Nla III eluted at approximately 0.4M NaCl. The fractions containing the Nla III endonuclease peak were dialyzed into buffer B and applied to a 2.5×4 cm heparin-sepharose column equilibrated in buffer B. The column was washed with 40 ml buffer B, then a 200 ml linear gradient from 0.1M to 1.1M NaCl in buffer A was applied. 4 ml fractions were collected and the Nla III peak localized by assaying as above. The Nla III eluted between 0.3M to 0.5M NaCl. The Nla III containing fractions were dialyzed into buffer C (20 mM KPO$_4$ pH6.0, 10 mM 2-mercaptoethanol, 0.1 mM EDTA, 0.1M NaCl) and applied to a 1.5×10 cm CM-sepharose column equilibrated in buffer C. The column was washed with 30 ml buffer C, then a 180 ml linear gradient from 0.1M to 1.1M NaCl was applied and a 3 ml fractions collected. The Nla III was found to elute at approximately 0.3M NaCl. The fractions containing maximum Nla III activity were applied to a G-75 column equilibrated in buffer D (20 mM KPO$_4$ pH7.0, 10 mM 2-mercaptoethanol, 0.1 mM EDTA, 0.5M NaCl) and 500 ml buffer D applied to the column. The fractions containing maximal Nla III activity eluted from 220 to 250 ml and were dialyzed into Nla III storage buffer (10 mM Tris-HCl pH 7.4, 200 mM KCl, 0.1 mM EDTA, 1 mM DTT, 200 ug/ml BSA, 50% glycerol) and stored at −20° C. The Nla III endonuclease obtained from this purification is substantially pure and free of non-specific endonuclease and exonucleases, and is entirely free from contamination with Nla I, Nla II and Nla IV endonucleases.

What is claimed is:

1. Isolated DNA consisting essentially of a nucleotide sequence which encodes the Nla III restriction endonuclease endogenous to *N. lactamica* NRCC 2118.

2. The isolated DNA of claim 1 further consisting essentially of a nucleotide sequence which encodes the Nla III methylase endogenous to *N. lactamica* NRCC 2118.

3. The isolated DNA of claim 1 or 2, wherein the isolated DNA is obtained from the plasmid pRM125RM 100c-4.

4. A recombinant vector into comprising a vector which a DNA segment coding for the Nla III endonuclease endogenous to *N. lactimica* NRCC 2118 has been inserted.

5. A recombinant vector comprising a vector into which the isolated DNA of claim 1 or 2 is inserted.

6. A host cell transformed with the recombinant vector of claim 4.

7. A host cell transformed with the recombinant vector of claim 5.

8. The transformed host of claim 5, wherein the host cell is selected from the group consisting of *E. coli* RR1, *E. coli* MM294 or *E coli* ER1398.

9. Recombinant Nla III restriction endonuclease which recognizes the DNA sequence CATG, which endonuclease is a) endogenous *N. lactamica* NRCC 2118, and, b) free of Nla I, Nla II and Nla IV.

10. A method of producing Nla III restriction endonuclease comprising culturing a host cell transformed with the vector of claim 4 under conditions suitable for expression of Nla III restriction endonuclease.

11. A method of producing Nla III restriction endonuclease comprising culturing a host cell transformed with the vector of claim 5 under conditions suitable for expression of Nla III restriction endonuclease.

12. The method of claim 10, wherein the recombinant vector comprises the plasmid pRM125RM 100c-4.

13. The method of claim 10, wherein the host is selected from the group consisting of *E. coli* RR1, *E. coli* MM294 or *E. coli* ER1398.

14. Recombinant Nla III restriction endonuclease produced by the method of claim 10.

* * * * *